United States Patent [19]

Fikentscher et al.

[11] Patent Number: 4,654,432
[45] Date of Patent: Mar. 31, 1987

[54] PREPARATION OF 2-(HYDROXYMETHYL)-ACRYLONITRILE AND 2-(HYDROXYMETHYL)-ACRYLATES

[75] Inventors: Rolf Fikentscher, Ludwigshafen; Erwin Hahn, Heidelberg; Alexander Kud, Enkenbach-Alsenborn; Alfred Oftring, Ludwigshafen, all of Fed. Rep. of Germany

[73] Assignee: BASF Aktiengesellschaft, Ludwigshafen, Fed. Rep. of Germany

[21] Appl. No.: 804,122

[22] Filed: Dec. 3, 1985

[30] Foreign Application Priority Data

Dec. 4, 1984 [DE] Fed. Rep. of Germany ....... 3444098

[51] Int. Cl.$^4$ .................... C07C 121/30; C07C 57/03
[52] U.S. Cl. .................... 558/357; 558/372; 558/451; 560/181; 558/20
[58] Field of Search .................... 560/183, 181; 568/840 B; 558/451, 357, 372

[56] References Cited

U.S. PATENT DOCUMENTS 3,066,165 11/1962 Rosenthal et al. .................. 560/183
3,499,024 3/1970 Morita et al. .................. 560/183 UX
3,743,669 7/1973 Hillman et al. .................. 560/60 X

OTHER PUBLICATIONS

Weygand/Hilgetag, Preparative Organic Chemistry, (1972), p. 954; John Wiley & Sons, N.Y.–London.

Primary Examiner—Joseph Paul Brust
Attorney, Agent, or Firm—Oblon, Fisher, Spivak, McClelland & Maier

[57] ABSTRACT 2-(hydroxymethyl)-acrylonitrile and 2-(hydroxymethyl)-acrylates of the formula

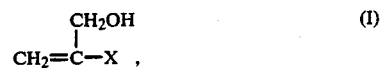

where X is —CN or

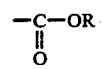

and R is unsubstituted or substituted alkyl, are prepared by reacting acrylonitrile or an acrylate with hydrated formaldehyde or a hemiacetal of formaldehyde in the presence of a tertiary amine as a catalyst.

14 Claims, No Drawings

PREPARATION OF 2-(HYDROXYMETHYL)-ACRYLONITRILE AND 2-(HYDROXYMETHYL)-ACRYLATES

U.S. Pat. No. 3,743,669 discloses the preparation of 2-(1-hydroxyalkyl)-acrylonitriles and 2-(1-hydroxyalkyl)-acrylates of the general formula

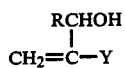 (III)

where Y is, inter alia, —CN or

and R and R$^1$ are each alkyl or aryl. The compounds of formula III are prepared by reacting acrylonitrile or an acrylate of the formula CH$_2$=CH—Y with an aldehyde of the formula RCHO, where Y and R have the meanings stated for formula III, in the presence of a tertiary amine as a catalyst, at from 0° to 200° C.

According to U.S. Pat. No. 2,601,650, 2-(hydroxymethyl)-acrylonitriles are obtained by reacting compounds of the formula

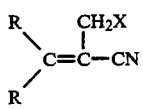 (IV)

with bases in an aqueous medium. In formula IV, R is H or alkyl of not more than 3 carbon atoms, and X is halogen.

In the process described in U.S. Pat. No. 3,066,165, 2-(hydroxymethyl)-acrylates are prepared by reacting propargylalcohol with carbon monoxide in the presence of nickel tetracarbonyl and acetic acid in an aqueous medium to give 2-(hydroxymethyl)-acrylic acid, and then esterifying the latter with an alcohol of 1 to 8 carbon atoms.

Some of the processes described above for the preparation of 2-(hydroxymethyl)-acrylonitrile or 2-(hydroxymethyl)-acrylates are relatively involved and either employ expensive starting materials or an expensive procedure or give the desired hydroxymethyl compounds only in poor yield.

It is an object of the present invention to provide an improved process for the preparation of 2-(hydroxymethyl)-acrylonitrile and 2-(hydroxymethyl)-acrylates.

We have found that this object is achieved, in accordance with the invention, by a process for the preparation of 2-(hydroxymethyl)-acrylonitrile and 2-(hydroxymethyl)-acrylates of the formula

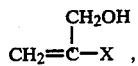 (I)

where X is —CN or

R is C$_1$-C$_{18}$-alkyl, —(CH$_2$)$_n$—OH,

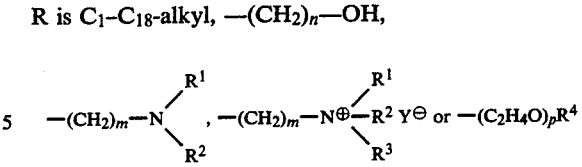

R$^1$ and R$^2$ are each —CH$_3$ or —C$_2$H$_5$,
R$^3$ is —H, —CH$_3$, —C$_2$H$_5$ or CH$_2$C$_6$H$_5$
R$^4$ is C$_1$-C$_{18}$-alkyl,
n is from 2 to 4,
m is from 2 to 5,
p is from 1 to 80 and
Y$^\ominus$ is Cl$^-$, Br$^-$, SO$_4{}^{2-}$, PO$_4{}^{3-}$, CH$_3$OSO$_3{}^-$, C$_2$H$_5$OSO$_3{}^-$, CH$_3$COO$^-$ or HCOO$^-$,
wherein a compound of the formula

 (II)

where X has the meanings stated for formula I, is reacted with hydrated formaldehyde or a hemiacetal of formaldehyde derived from a C$_1$-C$_6$-alcohol, in the presence of a tertiary amine as a catalyst.

Suitable compounds of the formula II are acrylonitrile and acrylates. In formula II,
X is CN or

R is C$_1$-C$_{18}$-alkyl, —(CH$_2$)$_n$—OH,

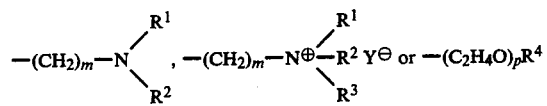

R$^1$ and R$^2$ are each —CH$_3$ or —C$_2$H$_5$,
R$^3$ is —H, —CH$_3$, —C$_2$H$_5$ or

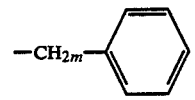

R$^4$ is C$_1$-C$_{18}$-alkyl,
n is from 2 to 4,
m is from 2 to 5,
p is from 1 to 80 and
Y$^\ominus$ is Cl$^-$, Br$^-$, SO$_4{}^{2-}$, PO$_4{}^{3-}$, CH$_3$OSO$_3{}^-$, C$_2$H$_5$OSO$_3{}^-$, CH$_3$COO$^-$ or HCOO$^-$,
Examples of C$_1$-C$_{18}$-alkyl acrylates are methyl acrylate, ethyl acrylate, n-propyl acrylate, isopropyl acrylate, n-butyl acrylate, isobutyl acrylate, tert.-butyl acrylate, n-octyl acrylate, isooctyl acrylate, 2-ethylhexyl acrylate, cyclopentyl acrylate, cyclohexyl acrylate, lauryl acrylate, palmityl acrylate and stearyl acrylate. Formula II furthermore embraces hydroxyethyl acrylate, hydroxypropyl acrylate and hydroxybutyl acrylate, all possible isomeric glycols or mixtures of these being suitable for hydroxyalkyl acrylates derived from C$_3$-C$_4$-glycols as well as dimethylaminoethyl acrylate, diethylaminoethyl acrylate, dimethylaminopropyl acrylate, diethylaminopropyl acrylate, dimethylaminobutyl acrylate, diethylaminobutyl acrylate, dimethylaminoneopentyl acrylate, diethylaminoneopentyl acrylate and the neutralized and quaternized dialkylaminoalkyl acrylates. Examples of suitable quaternization agents are dimethyl sulfate, diethyl sulfate, methyl chloride, ethyl chloride, methyl bromide, ethyl bromide and benzyl chloride. The salts of the dimethylaminoalkyl acrylates are obtained by neutralization with hydrochloric acid, hydrobromic acid, sulfuric acid, phosphoric acid or a saturated carboxylic acid, such as formic acid or acetic acid.

Compounds of the formula II where

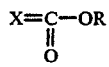

and R is $-(C_2H_4O)_pR^4$, $R^4$ is $C_1-C_{18}$-alkyl and p is 1 to 80 or, for example, methoxyethyl acrylate, ethoxyethyl acrylate, lauryloxytrioxyethyl acrylate and methoxypolyoxyethyl acrylates containing from 1 to 80, preferably from 3 to 30, oxyethyl groups. Among the compounds of the formula II, acrylonitrile, methyl acrylate, ethyl acrylate, 2-ethylhexyl acrylate, hydroxyethyl acrylate and hydroxybutyl acrylate are preferably used.

Acrylonitrile and the stated acrylates are converted at from 0° to 150° C., preferably from 0° to 70° C., in an aqueous medium at pH 7-13, preferably 8-10, in the presence of a tertiary amine as a catalyst. The pH of the reaction mixture is adjusted by adding the tertiary amine which acts as the catalyst. If the aqueous formaldehyde solution has a very low pH, it is advisable to neutralize it with a base before the reaction, for example with sodium hydroxide solution, potassium hydroxide solution, sodium carbonate, calcium hydroxide or barium hydroxide. The formaldehyde is preferably used in the form of an aqueous solution which contains from 5 to 40% by weight of formaldehyde, or in the form of the hemiacetal. However, it is also possible to react gaseous formaldehyde with the compounds of the formula II in a reactor; in this case, however, the reaction has to be carried out in the presence of water in order for hydration of the formaldehyde to take place. Preferably, commerical concentrated aqueous solutions of formaldehyde are used. Formaldehyde may also be employed in the form of an alcoholic solution or as the pure hemiacetal. Alcohols are preferably used as solvents and as hemiacetal formers from methanol, ethanol, n-propanol, isopropanol, butanols, hexanol, cyclohexanol, ethylene glycol, propylene glycol, methyl glycol, ethyl glycol and hexanediol.

The reaction is preferably carried out using homogeneous mixture. Where the acrylates used are sparingly soluble in water, it is advisable to carry out the reaction in the presence of a solvent which is inert to the reactants and which is miscible both with the reactants and with water. As much as 1000, preferably from 10 to 200 parts by weight of an inert solvent can be used per 100 parts by weight of the mixture of the compound of the formula II and formaldehyde. Examples of such solvents are all water-miscible alcohols, such as methanol, ethanol, isopropanol, n-propanol, butanol, ethylene glycol, propylene glycol, partially or completely etherified $C_2-C_4$-glycols or polyethylene glycols having a molecular weight of not more than 800, and dioxane, tetrahydrofuran and acetonitrile. In some cases, it may also be advantageous to use a mixture of several solvents, for example a mixture of tetrahydrofuran and methanol, or of acetonitrile, dioxane and methanol.

The reaction is carried out in the presence of a tertiary amine, both open-chain aliphatic amines and cyclic tertiary amines being suitable. Examples of these are trimethylamine, triethylamine, tri-n-propylamine, triisopropylamine, tributylamine, triisobutylamine, tri-n-pentylamine, N-methyldiiso-propylamine, N,N-diethylisopropylamine, N,N-dimethylethylamine, N,N-dimethylisopropylamine, tri-2-ethylhexylamine, N-methyldiethyamine, N,N-dimethyl-n-propylamine, N,N-dimethyl-n-butylamine, N,N-dimethylisobutylamine, N,N-dimethyl-(2-ethylhexyl)amine, N,N-diisopropyl-(2-ethylhexyl)-amine, N,N-di-n-butyl-(2-ethylhexyl)-amine, N-methyldi-(2-ethylhexyl)-amine, N-n-butyl-di-(2-ethylhexyl)-amine, N-isobutyl-di-(2-ethylhexyl)amine, 1,4-diazabicyclo[2.2.2]-octane, pyrrocoline and quinolidine. From 0.1 to 10, preferably from 3 to 8, parts by weight of a tertiary amine are used per 100 parts by weight of the mixture of the compound of the formula II and formaldehyde. The reaction is preferably carried out in the presence of 1,4-diazabicyclo[2.2.2]octane, pyrrocoline or quinolidine. As a rule, the compound of the formula II and formaldehyde are reacted with one another in the equimolar amounts. However, for technical reasons it may be necessary to use an excess of one or other of the components. For example, the molar ratio of formaldehyde to the compound of the formula II may be varied from 20:1 to 1:2, preferably from 5:1 to 0.75:1. The reaction is usually carried out under atmospheric pressure but may also be effected under reduced or superatmospheric pressure. Superatmospheric pressure is necessary in particular when the reaction is carried out at above 100° C.

The products prepared by the novel process, ie. 2-(hydroxymethyl)-acrylonitrile and 2-(hydroxymethyl)-acrylates of the formula I above, are useful intermediates and, because of their structure, are employed in particular as monomers for the preparation of polymers.

EXAMPLE 1

258 g (3 moles) of methyl acrylate, 225 g (3 moles) of 40% strength aqueous formaldehyde and 20 g (0.17 mole) of 1,4-diazabicyclo[2.2.2]octane and 250 ml of methanol are mixed in a flask, which is then closed and shaken on a machine for 48 hours at room temperature. The pH of the reaction mixture is about 9. When the reaction is completed, concentrated hydrochloric acid is added to the reaction mixture in an amount sufficient to bring the pH to 5.5. 400 ml of diethyl ether are then added, the mixture is shaken vigorously and the phases are then allowed to separate. The organic phase is removed, washed with 100 ml of a saturated sodium chloride solution and dried over sodium sulfate, after which the organic solvent is distilled off and the residue is subjected to fractional distillation. 261 g (75% of theory) of methyl 2-(hydroxymethyl)-acrylate are obtained in the form of a colorless liquid of boiling point 72°-76° C. under 0.3 mbar.

The reaction can be carried out similarly and with similar yields using tetrahydrofuran instead of methanol.

EXAMPLE 2

159 g (3 moles) of acrylonitrile, 225 g (3 moles) of a 40% strength aqueous solution of formaldehyde and 12.5 g (0.11 mole) of 1,4-diazabicyclo[2.2.2]octane are mixed in a flask, and the mixture is stirred for 48 hours at room temperature. The pH during the reaction is about 9. When the reaction is complete, the readily volatile components are distilled off under 14 mbar, and the residue is dissolved in 400 ml of diethyl ether. The ether solution is washed with 70 ml of an 8% strength aqueous hydrochloric acid and then with 70 ml of a saturated aqueous sodium chloride solution and dried over sodium sulfate. The ether is distilled off and the residue is subjected to fractional distillation under 0.3 mbar. 164 g (66% of theory) of 2-(hydroxymethyl)-acrylonitrile are obtained in the form of a colorless product at from 84° to 86° C. under this pressure.

EXAMPLE 3

100 ml of ethanol are added to 184 g (1 mole) of 2-ethylhexyl acrylate, 75 g (1 mole) of a 40% strength aqueous formaldehyde and 11.4 g (0.1 mole) of 1,4-diazabicyclo [2.2.2]octane (abbreviated to DABCO below), and the mixture is heated at 50° C. for 36 hours. The pH of the reaction mixture at the beginning of the reaction is 9.7.

When the reaction is complete, the pH is brought to 5 with concentrated hydrochloric acid and the mixture is extracted with 200 ml of diethyl ether.

The organic phase is washed with 50 ml of water and dried over sodium sulfate, and the organic solvent and other readily volatile components are distilled off to give 152 g (71% of theory) of 2'-ethylhexyl 2-(hydroxymethyl)-acrylate as a colorless liquid.

EXAMPLE 4

26 g (0.2 mole) of hydroxypropyl acrylate, 15 g (0.2 mole) of 42.5% strength formalin, 2 g (17.8 millimoles) of DABCO and 20 g of ethanol are stirred thoroughly for 72 hours at room temperature.

Thereafter, the pH is brought to 5 with semiconcentrated hydrochloric acid and the mixture is extracted by shaking with 3 times 40 ml of dichloromethane.

The combined organic phases are washed with 30 ml of water and dried over sodium sulfate, after which the solvent and other volatile components are removed under reduced pressure.

26 g (81% of theory) of 3'-hydroxypropyl 2-(hydroxymethyl)-acrylate remain as a pale yellow liquid.

EXAMPLE 5

68.4 g (0.4 mole) of N,N-diethylaminoethyl acrylate, 32 g (0.4 mole) of 40% strength formalin and 4.0 g (35.0 millimoles) of DABCO are stirred thoroughly for 50 hours at 25° C.

Thereafter, the pH is brought to 6 with semiconcentrated hydrochloric acid and the mixture is extracted by shaking with 3 times 50 ml of dichloromethane. The organic phase is washed with 50 ml of a saturated sodium chloride solution and dried over sodium sulfate, after which volatile components are removed under reduced pressure.

61 g (75% of theory) of 2'-diethylaminoethyl 2-(hydroxymethyl)-acrylate remain.

EXAMPLE 6

43 g (0.5 mole) of methyl acrylate and 3 g (26.7 millimoles) of DABCO are added to a solution of 11 g (0.36 mole) of anhydrous monomeric formaldehyde in 100 ml of absolute ethanol, and the mixture is left to stand for 72 hours at room temperature. Volatile components are then removed under reduced pressure from a water pump, the residue is taken up in 100 ml of diethyl ether, and the ether solution is washed with 20 ml of a 10% strength aqueous hydrochloric acid and with 30 ml of a saturated aqueous sodium chloride solution. The organic phase is dried over sodium sulfate and the solvent is then removed under reduced pressure from a water pump, after which the residue is subjected to fractional distillation as described in Example 1. 25 g (59% of theory) of methyl 2-(hydroxymethyl)-acrylate are obtained.

EXAMPLE 7

86 g (1 mole) of methyl acrylate, 75 g (1 mole) of 40% strength formaldehyde and 7 g (0.06 mole) of DABCO are mixed in a flask, and the mixture is then stirred throughly for 72 hours.

Working up is carried out by a method similar to that described in Example 1, and 48 g (41% of theory) of methyl 2-(hydroxymethyl)-acrylate are obtained.

When the experiment is carried out in a similar manner, using triethylamine instead of DABCO, a yield of 31% of theory is obtained.

EXAMPLE 8

100 g (1 mole) of ethyl acrylate, 113 g (1.5 moles) of 40% strength aqueous formaldehyde and 7 g (62 millimoles) of DABCO and 100 ml of acetonitrile are mixed in a flask. The pH of the reaction mixture is initially 8.9.

The mixture is stirred thoroughly for 40 hours at 50° C., after which semiconcentrated hydrochloric acid is added to the reaction mixture in an amount sufficient to bring the pH to 5.0. 200 ml of diethyl ether are then added, the mixture is shaken vigorously and the organic phase is separated off, washed with 50 ml of a saturated, aqueous sodium chloride solution and dried over sodium sulfate. The organic solvent is distilled off, and the residue is then subjected to fractional distillation.

86 g (66% of theory) of ethyl 2-(hydroxymethyl)-acrylate of boiling point 84°–86° C. are obtained under 0.4 mbar.

EXAMPLE 9

When 130 g (1 mole) of cyclohexanol formaldehyde hemiacetal in 100 g of cyclohexanol and 86 g (1 mole) of methyl acrylate are reacted, 8 g (71.4 millimoles) of 1,4-diazabicyclo [2.2.2]octane are added and the mixture is stirred for 70 hours at 25° C., methyl 2-(hydroxymethyl)-acrylate is obtained in a yield of 45% (according to HPLC).

We claim:

1. A process for the preparation of 2-(hydroxymethyl)-acrylonitrile and 2-(hydroxymethyl)-acrylates of the formula:

where X is CN or

R is $C_1$–$C_{18}$-alkyl, —$(CH_2)_n$—OH,

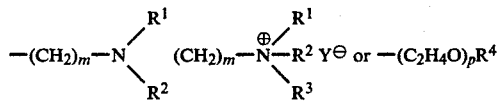

or $-(C_2H_4O)_pR^4$ $R^1$ and $R^2$ are each $-CH_3$ or $-C_2H_5$,
$R^3$ is $-H$, $-CH_3$, $-C_2H_5$ or $-CH_2C_6H_5$,
$R^4$ is $C_1-C_{18}$-alkyl,
n is from 2 to 4,
m is from 2 to 5,
p is from 1 to 80 and
$Y^\ominus$ is $Cl^-$, $Br^-$, $SO_4^{2-}$, $PO_4^{3-}$, $CH_3OSO_3^-$, $C_2H_5OSO_3^-$, $HC_3COO^-$ or $CHOO^-$, which comprises:

reacting a compound of the formula:

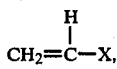  (II)

where X is as defined above, with hydrated formaldehyde or a formaldehyde hemiacetal, prepared by the reaction of formaldehyde with a $C_1-C_6$-alcohol, or mixtures of the hydrated formaldehyde and hemiacetal, in the presence of a tertiary amine as a catalyst at a temperature of from 0° to 150° C.

2. The process of claim 1, wherein said reaction is conducted in the presence of water or an alcohol at a pH ranging from 8 to 10.

3. The process of claim 1, wherein said reaction is conducted in the presence of an inert solvent which is miscible with the reactants and with water.

4. The process of claim 1, wherein the medium of said reaction comprises from 10 to 200 parts by weight of a $C_1-C_4$-alcohol, dioxane, tetrahydrofuran, dimethylformamide, acetonitrile, or mixtures thereof per 100 parts by weight of a mixture of the compound of formula II and hydrated formaldehyde or formaldehyde hemiacetal, or mixtures thereof.

5. The process of claim 1, wherein the medium of said reaction comprises from 0.1 to 10 parts by weight of said tertiary amine catalyst per 100 parts by weight of the mixture of the compound of formula II with hydrated formaldehyde or formaldehyde hemiacetal or mixtures thereof.

6. The process of claim 1, wherein said tertiary amine catalyst is a member selected from the group consisting of trimethylamine, triethylamine, tri-n-propylamine, triisopropylamine, tributylamine, triisobutylamine, tri-n-pentylamine, N-methyldiisopropylamine, N,N-diethylisopropylamine, N,N-dimethylethylamine, N,N-dimethylisopropylamine, tri-2-ethylhexylamine, N-methyldiethylamine, N,N-dimethyl-n-propylamine, N,N-dimethyl-n-butylamine, N,N-dimethylisobutylamine, N,N-dimethyl-(2-ethylhexyl)amine, N,N-diisopropyl-(2-ethylhexyl)amine, N,N-di-n-butyl-(2-ethylhexyl)-amine, N-methyldi-(2-ethylhexyl)-amine, N-n-butyl-di-(2-ethylhexyl)amine, N-isobutyl-di-(2-ethylhexyl)-amine, 1,4-diazabicyclo[2,2,2]-octane, pyrrocoline and quinolidine.

7. The process of claim 6, wherein said tertiary amine catalyst is 1,4-diazabicyclo[2,2,2]octane, pyrrocoline or quinoldine.

8. The process of claim 1, wherein said hemiacetal is the hemiacetal of formaldehyde with methanol.

9. The process of claim 1, wherein said $C_1-C_{18}$-alkylacrylate reactant is a member selected of the group consisting of methyl acrylate, ethyl acrylate, n-propyl acrylate, isopropyl acrylate, n-butyl acrylate, isobutyl acrylate, t-butyl acrylate, n-octyl acrylate, isooctyl acrylate, 2-ethylhexyl acrylate, cyclopentyl acrylate, cyclohexyl acrylate, lauryl acrylate, palmityl acrylate and stearyl acrylate.

10. The process of claim 1, wherein said hydroxyalkyl acrylate reactant is a member selected from the group consisting of hydroxyethyl acrylate, hydroxypropyl acrylate.

11. The process of claim 1, wherein said alkylaminoalkyl acrylate reactant is a member selected from the group consisting of dimethylaminoethyl acrylate, diethylaminoethyl acrylate, dimethylaminopropyl acrylate, diethylaminopropyl acrylate, dimethylaminobutyl acrylate, diethylaminobutyl acrylate, dimethylaminoneopentyl acrylate, and diethylaminoneopentyl acrylate.

12. The process of claim 1, wherein said $C_1-C_6$-alcohol is a member selected from the group consisting of methanol, ethanol, n-propanol, isopropanol, butanols, hexanol, cyclohexnaol, propylene glycol, methyl glycol, ethyl glycol and hexanediol.

13. The process of claim 1, wherein the molar ratio of the formaldehyde reactant to the reactant of formula II ranges from 20:1 to 1:2.

14. The process of claim 13, wherein said ratio ranges from 5:1 to 0.75:1.

* * * * *